US010800966B2

(12) United States Patent
Bliznyuk et al.

(10) Patent No.: US 10,800,966 B2
(45) Date of Patent: Oct. 13, 2020

(54) ORGANIC SCINTILLATORS DERIVED FROM PYRAZOLINE

(71) Applicants: CLEMSON UNIVERSITY, Clemson, SC (US); Institute of Organic Chemistry, National Academy of Science of Ukraine, Kiev (UA)

(72) Inventors: Valery N. Bliznyuk, Clemson, SC (US); Ayman F. Seliman, Clemson, SC (US); Timothy A. DeVol, Clemson, SC (US); Nadezhda A. Derevyanko, Kiev (UA); Alexander A. Ishchenko, Kiev (UA)

(73) Assignees: Clemson University Research Foundation, Clemson, SC (US); Institute of Organic Chemistry, National Academy of Science of Ukraine, Kiev (UA)

( * ) Notice: Subject to any disclaimer, the term of this patent is extended or adjusted under 35 U.S.C. 154(b) by 612 days.

(21) Appl. No.: 15/493,846

(22) Filed: Apr. 21, 2017

(65) Prior Publication Data

US 2017/0306220 A1    Oct. 26, 2017

Related U.S. Application Data

(60) Provisional application No. 62/326,391, filed on Apr. 22, 2016.

(51) Int. Cl.
  *C09K 11/06* (2006.01)
  *C09K 11/02* (2006.01)
  *C07D 231/06* (2006.01)

(52) U.S. Cl.
  CPC .......... *C09K 11/025* (2013.01); *C07D 231/06* (2013.01); *C09K 11/06* (2013.01);
  (Continued)

(58) Field of Classification Search
  CPC ...................................... C09K 11/06
  See application file for complete search history.

(56) References Cited

U.S. PATENT DOCUMENTS

| 2,985,593 A | * | 5/1961 | Broderick | ............ | C07D 231/06 |
| | | | | | 252/301.17 |
| 2002/0043656 A1 | * | 4/2002 | Shershukov | ......... | C07D 471/06 |
| | | | | | 252/586 |

OTHER PUBLICATIONS

Sandler. Fluorescence Spectral Study of Wavelength Shifters for Scintillation Plastics. Jouranl of Chemical Physics. vol. 39, No. 4. Aug. 15, 1963. p. 1062-1067.*

(Continued)

*Primary Examiner* — Matthew E. Hoban
(74) *Attorney, Agent, or Firm* — Dority & Manning, P.A.

(57) ABSTRACT

Pyrazoline-based fluorophores and plastic scintillators incorporating the fluorophores are described. The fluorophores include 1,3,5-triaryl substituted pyrazolines. A fluorophore of a plastic scintillator can be a 1-phenyl-4,5-1H-dihydroyrazole having the structure:

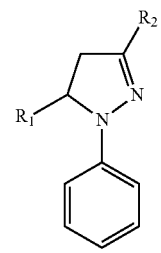

in which $R_1$ and $R_2$ are independently selected from a heteroaryl group including one or more of an oxygen, selenium or sulfur atom in the ring; an aryl halide group; or (Continued)

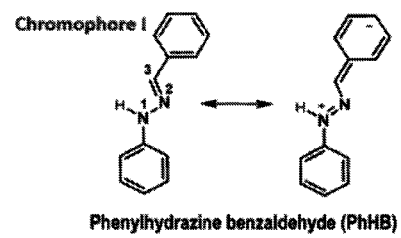

Phenylhydrazine benzaldehyde (PhHB)

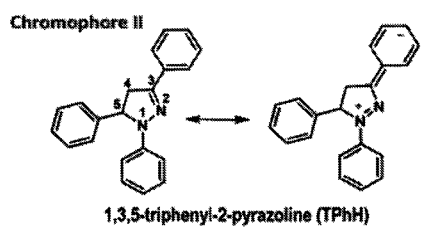

1,3,5-triphenyl-2-pyrazoline (TPhH)

a phenyl alkyl including a C1 to C18 saturated or unsaturated alkyl that optionally includes a reactive functionality.

12 Claims, 7 Drawing Sheets

(52) U.S. Cl.
CPC .................. *C09K 2211/1007* (2013.01); *C09K 2211/1014* (2013.01); *C09K 2211/1044* (2013.01)

(56) References Cited

OTHER PUBLICATIONS

Lavrushin. Synthesis of furan analogs of 1, 3, 5-triphenylpyrazoline derivatives. Chemistry of Heterocyclic Compounds May 1966, vol. 1, Issue 3, pp. 211-214.*
Lavrushin. Synthesis of thiophene analogs of 1, 3, 5-triphenylpyrazoline derivatives. Chemistry of Heterocyclic Compounds Sep. 1965, vol. 1, Issue 5, pp. 465-468.*
Schäferling, Michael. "The art of fluorescence imaging with chemical sensors." Angewandte Chemie International Edition 51.15 (2012): 3532-3554.
Hötzer B, Medintz IL, Hildebrandt N. Fluorescence in nanobiotechnology: sophisticated fluorophores for novel applications. Small. Aug. 6, 2012;8(15):2297-326.
Budakovsky, Sergey V., et al. "New effective organic scintillators for fast neutron and short-range radiation detection." IEEE Transactions on Nuclear Science 54.6 (2007): 2734-2740.
Zaitseva, Natalia, et al. "Plastic scintillators with efficient neutron/gamma pulse shape discrimination."Nuclear Instruments and Methods in Physics Research Section A: Accelerators, Spectrometers, Detectors and Associated Equipment 668 (2012): 88-93.
Yoshida, S., et al. "Ultra-violet wavelength shift for undoped CaF2 scintillation detector by two phase of liquid scintillator system in CANDLES." Nuclear Instruments and Methods in Physics Research Section A: Accelerators, Spectrometers, Detectors and Associated Equipment 601.3 (2009): 282-293.
Clapham, Bruce, and Andrew J. Sutherland. "Stille coupling reactions of 4-substituted-2, 5-diphenyloxazoles." The Journal of organic chemistry 66.26 (2001): 9033-9037.
Bliznyuk VN, Duval CE, Apul OG, Seliman AF, Husson SM, DeVol TA. High porosity scintillating polymer resins for ionizing radiation sensor applications. Polymer. Jan. 15, 2015;56:271-9.
Bliznyuk VN, Seliman AF, Husson SM, Chumanov G, DeVol TA. Fluorescence properties of fluor molecules confined within nanoscale pores in a polymer matrix. MRS Communications. Jun. 1, 2015;5(02):347-52.
Brouwer AM. Standards for photoluminescence quantum yield measurements in solution (IUPAC Technical Report). Pure and Applied Chemistry. Aug. 31, 2011;83(12):2213-28.
Stewart JJ. MOPAC: a semiempirical molecular orbital program. Journal of computer-aided molecular design. Mar. 1, 1990;4(1):1-03.
Seliman, Ayman F., et al. "Development of polymerizable 2-(1-naphthyl)-5-phenyloxazole scintillators for ionizing radiation detection." Journal of Materials Chemistry C 3.27 (2015): 7053-7061.
Gómez, Juan Carlos Cobas, Michael Bernstein, and Stanislav Sýkora. "An Integrated Approach to Structure Verification Using Automated Procedures." Structure Elucidation in Organic Chemistry: The Search for the Right Tools (2014): 445-492.

* cited by examiner

ORGANIC SCINTILLATORS DERIVED FROM PYRAZOLINE

CROSS REFERENCE TO RELATED APPLICATION

This application claims filing benefit of U.S. Provisional Patent Application Ser. No. 62/326,391 having a filing date of Apr. 22, 2016, which is incorporated herein by reference.

STATEMENT REGARDING FEDERALLY SPONSORED RESEARCH OR DEVELOPMENT

This invention was made with government support under grant # HDTRA1-12-1-0012 awarded by DOD/DTRA. The government has certain rights in the invention.

BACKGROUND

Organic fluorescent materials find increasing application in physics, chemistry and biology. Fluorophores, i.e., organic materials exhibiting re-emission capability with optical absorption ranges in the ultra-violet (UV) and near UV, are suitable for detection of different types of ionizing radiation including gamma rays, alpha particles, beta particles and neutrons. While fluorophores belong to several different classes of organic compounds, those with the highest luminosity are aromatic hydrocarbons constituted with some combination of condensed or bonded ring systems. Three main classes of organic fluorescent materials known as scintillators are single crystals, liquids and plastics. In the first class, the fluorophores are present in the pure bulk, crystallized form, which makes the materials rather expensive but with a superior scintillating performance. In liquid and plastic scintillators, on the other hand, fluorophores are dissolved as individual molecules held in an organic matrix. As a result of more than sixty years of research in the field, a number of crystalline, liquid and plastic scintillators have been developed with good luminescent characteristics.

From a practical viewpoint plastic scintillators are more promising than other forms as they are inexpensive, do not incorporate volatile or hazardous liquids (and therefore do not have to be encapsulated) and have better environmental stability. Moreover, plastic scintillators have attracted attention as having shown the capability of a pulse shape discrimination effect, allowing for the possibility of distinguishing between different types of radiation, e.g., neutron and gamma radiation. Though fabrication of plastic scintillators is relatively more difficult and usually requires several preparation steps (i.e., mixing, polymerization, casting, polishing), all of these steps are well known and can be easily adjusted for a particular application.

Unfortunately, in order to obtain a high quality scintillator, it is not sufficient when developing plastic scintillators to develop only a fluorophore with good photoluminescence characteristic. Interaction with the matrix and initial radioluminescence of the system excitation can be even more important. Upon initial absorption, the absorbed (deposited) energy of the radiation must be transferred through the polymer matrix to the fluorophores radiatively or nonradiatively via so called Förster resonance energy transfer (FRET) process.

Scintillation efficiency of plastic fluorophores is determined by several factors. Among them are the degree of spectral overlap of the radiation-absorbing polymer matrix with the light-emitting fluorophore molecules, the degree of the emission spectra overlap with the absorption of the photodetector, and the photoluminescence quantum yield (QY) of the fluorophore. Ideally, all three conditions are well satisfied. One approach that has been taken for scintillation efficiency enhancement is utilization of two organic fluorophores in a single matrix. One fluorophore is selected for excitation transfer from the matrix after capturing the ionizing radiation energy, and the second one is selected for the highest QY and the emission wavelength close to the maximum of the photodetector spectral sensitivity.

New fluorophores and scintillators that exhibit useful photoluminescence characteristics would be of benefit in the art. Plastic scintillators that can efficiently incorporate the fluorophores in polymer matrices would be particularly beneficial.

SUMMARY

According to one embodiment, disclosed are plastic scintillators incorporating pyrazoline-based fluorophores in a polymer matrix. For instance, a plastic scintillator can include a 1,3,5-triaryl substituted pyrazoline compound incorporated in a polymeric matrix. In one embodiment, the pyrazoline-based fluorophore of the plastic scintillator can be a 1-phenyl-4,5-1H-dihydroyrazole having the following general structure:

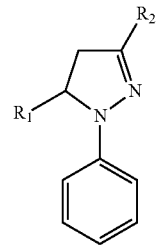

in which $R_1$ and $R_2$ are independently selected from a heteroaryl group including one or more of an oxygen, selenium, or sulfur atom in the ring; an aryl halide group; or a phenyl alkyl including a C1 to C18 saturated or unsaturated alkyl that optionally includes a reactive functional group.

Also disclosed are pyrazoline-based fluorophores having the following general structure:

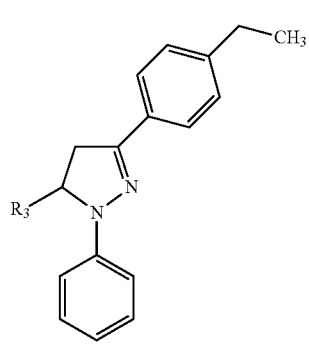

in which $R_3$ is an aryl halide group or a phenyl alkyl including a C1 to C18 saturated or unsaturated alkyl that optionally includes a reactive functional group.

BRIEF DESCRIPTION OF THE FIGURES

A full and enabling disclosure of the present subject matter, including the best mode thereof to one of ordinary skill in the art, is set forth more particularly in the remainder of the specification, including reference to the accompanying figures in which.

Figure 1:
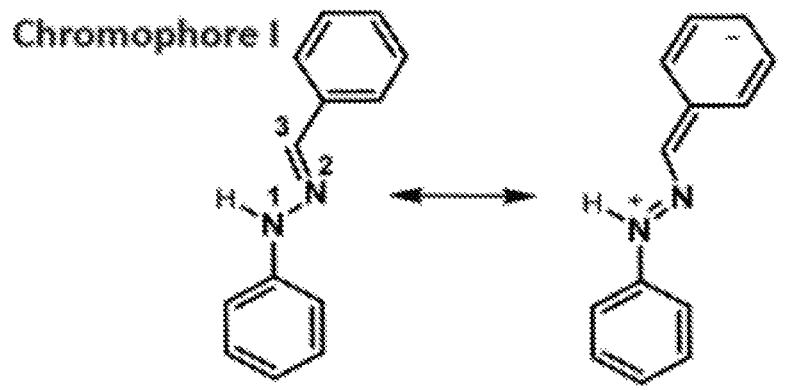
FIG. 1 schematically illustrates the two chromophore units of 1,3,5-triaryl substituted pyrazoline compounds disclosed herein.
Figure 1:
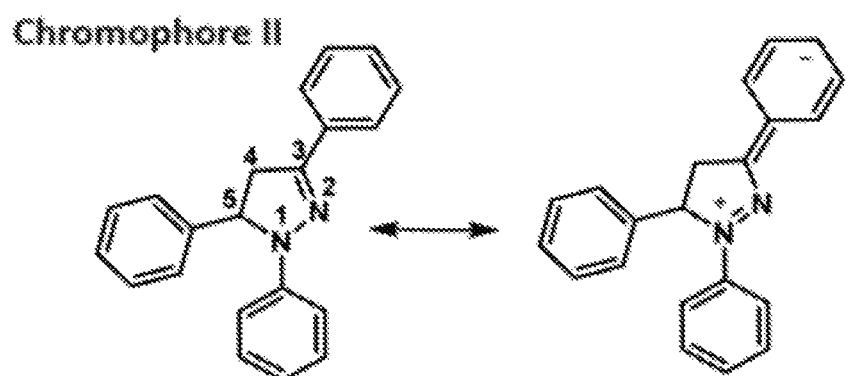

Repeat use of reference characters in the present specification and drawings is intended to represent the same or analogous features or elements of the present invention.

DETAILED DESCRIPTION

Reference will now be made in detail to various embodiments of the disclosed subject matter, one or more examples of which are set forth below. Each embodiment is provided by way of explanation of the subject matter, not limitation thereof. In fact, it will be apparent to those skilled in the art that various modifications and variations may be made in the present disclosure without departing from the scope or spirit of the subject matter. For instance, features illustrated or described as part of one embodiment, may be used in another embodiment to yield a still further embodiment.

In general, the present disclosure is directed to pyrazoline-based fluorophore compounds and plastic scintillators that can incorporate the pyrazoline-based fluorophore compounds. Beneficially, the disclosed fluorophores can be combined with a polymer matrix to form a plastic scintillator that exhibits bright fluorescence for use in one embodiment in radiation detection and measurement. Disclosed compounds can show superior performance to previously known fluorophores when combined with a polymer matrix (e.g., a styrene-based matrix or a polyvinyl-based matrix) in plastic scintillators.

In one particular embodiment, the fluorophores can be utilized for detection of ionizing radiation including alpha particles, beta particles, gamma rays, neutrons, or combinations thereof and can demonstrate superior photoluminescent brightness and high luminosity efficiency in comparison to existing commercially used fluorophores (e.g., 2-(1-naphthyl)-5-phenyloxazole (αNPO), 9,10-diphenylanthracene, etc.) in response to ionizing radiation.

The fluorophores are 1,3,5-triaryl substituted pyrazoline compounds that, in one embodiment, can be a heteroatom and/or aryl halide substituted pyrazoline derivative compound. More specifically, a plastic scintillator can incorporate a fluorophore having the following general structure:

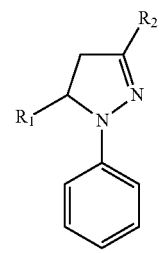

in which $R_1$ and $R_2$ are independently selected from a heteroaryl group; an aryl halide group; or a phenyl alkyl including a C1 to C18 saturated or unsaturated alkyl that optionally includes a reactive functional group.

By way of example, the $R_1$ group can be an aryl bromide or an aryl fluoride. An exemplary phenyl alkyl can include a phenyl alkene, and in one particular embodiment, a phenyl ethylene. In one embodiment, the substituted aryl groups of the fluorophore can be para-substituted, but this is not a requirement of the materials.

In some embodiments, the plastic scintillators can include materials as fluorophores that have been previously described, but have not been recognized as suitable for use as a fluorophore and in particular, as a component of a plastic scintillator. For instance, in one embodiment, a plastic scintillator can include a pyrazoline-based fluorophore including at least one heteroaryl group. For example, the pyrazoline-based fluorophore can have the following general structure:

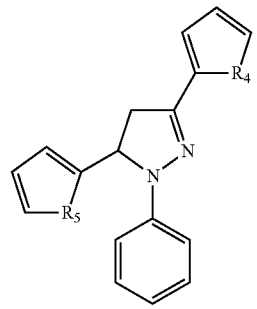

in which $R_4$ and $R_5$ are independently selected from sulfur, oxygen, selenium, or combinations thereof.

In other embodiments, disclosed are pyrazoline-based fluorophores that have not previously been reported. Fluorophores having the following general structure have been formed and characterized that, in one embodiment, can be advantageously incorporated in a plastic scintillator:

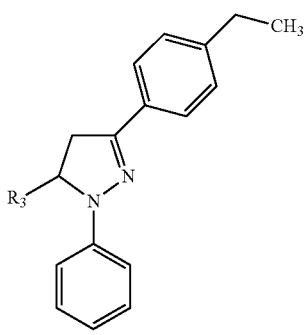

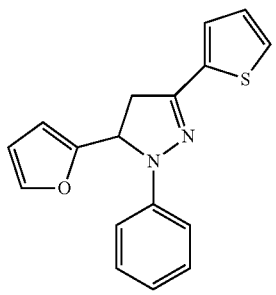

in which $R_3$ is an aryl halide group (e.g., an aryl bromide or an aryl fluoride) or a phenyl alkyl including a C1 to C18 saturated or unsaturated alkyl that optionally includes a reactive functional group (e.g., a phenyl ethylene).

Representative embodiments of particular fluorophores encompassed herein include the following:

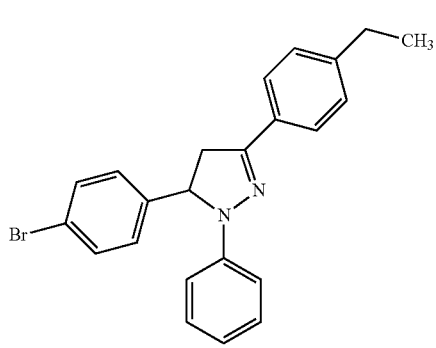

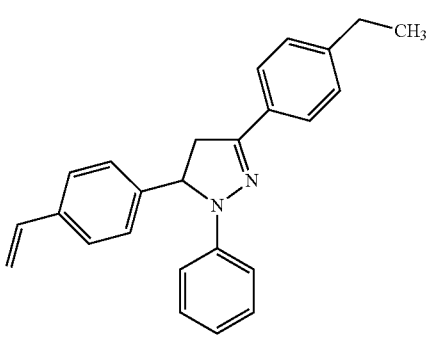

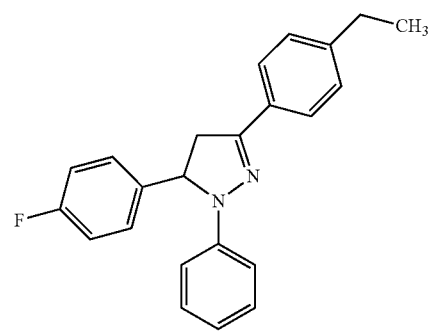

Disclosed fluorophores can be formed according to known chemistries, particular examples of which are described in more detail in the Examples section, below. As is known, pyrazolines can be synthesized in single or multi-step protocols with high yields, which makes them very attractive for various spectroscopic applications such as optical "whitening" luminescent dyes for plastics etc. For example, a Stille cross coupling reaction can be utilized, which can provide a route for further functionalization of an aryl halide fluorophore, for instance with a vinyl group as found in vPZ1 above. Substitution of the pyrazoline with a phenyl alkene can be beneficial in some embodiments, as it can provide functionality for further covalent bonding to the polymer matrix in formation of the plastic scintillator. This can dramatically improve chemical stability of the system while simultaneously improving the photoluminescence quantum yield.

Inclusion of a reactive functionality that can provide for bonding to the polymeric matrix is not limited to a vinyl functionality, and other reactive functionality in encompassed herein. For example, in other embodiments, the substituted pyrazoline can be substituted with allyl, thiol, epoxy, alkoxysilane groups or the like to provide a desired chemical reactivity to the fluorophore. For instance, following substitution of the pyrazoline with a phenyl alkene, the alkene group can be further derivatized to include another reactivity, e.g., epoxy or the like, that can then bond the fluorophore to the polymeric matrix.

When forming a plastic scintillator in which the fluorophore is bonded to the matrix, the crosslinking of the fluorophore to a component of the matrix (e.g., pendant to a polymer backbone) can be carried out in a single or multi-step process. For instance, a fluorophore can be derivatized in a first step to include a reactive functionality (e.g., vinyl, epoxy, etc.) that can then, in a second step, react to form a covalent bond with a reactive functionality of the matrix. Alternatively, the fluorophore (e.g., a fluorophore including a vinyl or other reactivity), a component of the matrix (e.g., a polymer or reactive monomers and/or oligomers), and a bifunctional reactive component that exhibits reactivity to both the fluorophore and the matrix component (e.g., a monomeric bifunctional crosslinking agent) can be combined and form in a single step the polymeric matrix bonded to the fluorophore. For instance, the fluorophore can be copolymerized with a suitable monomer using chain or step polymerization formations.

Without wishing to be bound to any particular theory, it is believed that the hetero-substitution of the phenyl rings with halogens (e.g., F, Br), O, Se, and/or S atoms is an important factor influencing the emission yield of the pyrazoline-based molecules. Accordingly, in one embodiment, a fluorophore can include a substitution as may provide reactive functionality for further covalent bonding to a polymer matrix in conjunction with a hetero-substitution of that or another phenyl ring of the molecule.

Without wishing to be bound to any particular theory, it is believed that the excellent spectral and luminescence properties of the fluorophore compounds is due to the pyrazoline fragment of their structure. In particular, the substituted pyrazoline unit can include two independent chromophores: one absorbing in the UV with a broad absorption range close to the band gap energy of the polymer of the matrix that can provided enhanced FRET efficiency, and another one absorbing in the near-UV and emitting in the visible range of light with the emission wavelength at around 450 nm (i.e., close to the maximum sensitivity of standard PMT detectors) that can provide enhanced quantum emission efficiency. As such, the disclosed pyrazoline fluorophores can combine the properties of primary and secondary fluorophores within one molecular structure. Moreover, they can possess high thermal and optical stability.

This double chromophore architecture is illustrated in FIG. 1 by use of 1,3,5-triphenyl-2-pyrazoline (TPhH) as a model compound. TPhH has a representative structure that can make it convenient for modeling the properties of the disclosed fluorophores as a whole. TPhH possesses two $\pi$-$\pi$* transitions. A long-wavelength transition originates from the conjugated bonds system spreading from the N(1) nitrogen atom to para substituted carbon in the benzene ring in position 3 (chromophore I) as shown in FIG. 1. The N(1) atom is acting as an auxochrome donating its unshared electron pair to the conjugation system. This allows formation of a bipolar structure in the first excited singlet state. The electron structure of the chromophore I is similar to that of its simplest analog phenylhydrazine benzaldehyde (PhHB). However, despite their structural similarity the latter compound has very low photoluminescence intensity while the TPhH (and its derivatives encompassed herein) is characterized with highly intensive emission in the blue range of light. This can be attributed to the enhancement of the structural rigidity of the core atoms N(1), N(2) and C(3) in the chromophore's structure due to bridging them with a saturated dimethylene fragment. At the same time the planarity of the whole structure is important to insure that the high photoluminescence quantum yield is preserved. The fact that fluorescence enhancement is due to the structural rigidity and is not a result of the electron structure modification is evident by practically identical absorption bands in both compounds (the difference in the absorption peak position is only 1 nm between TPhH and PhHB). The phenyl group adjacent to the N(1) atom also contributes to the conjugated structure of the chromophore I. This contribution is not significant however, as the group is tilted 39 degrees out from the conjugation plane. Such configuration has been proven by quantum chemical modeling and optimization of the ground state geometry for 1,3,5-triphenyl pyrazoline performed by the semi-empirical method Austin Model 1 (AM1) for the quantum calculation of molecular electronic structure in computational chemistry with a standard set of parameters and under application of the restricted open-shell Hartree-Fock method with Polak-Ribiere conjugate gradient algorithm.

Tilting of the group out from the conjugation plane is a result of a steric hindrance created by position 5 phenyl of the pyrazoline cycle. However, under electronic excitation the length of the N(1)-C(5) bond is increasing, which is evident from the reduction of its order from 0.894 to 0.872 within the above mentioned calculation technique. Thus, the steric hindrance is reduced in the excited state and the phenyl group is better adjusted to the conjugation system of the chromophore I (FIG. 1). This conclusion is supported by calculated enhancement of the N(1)-Ph bond order under transition from the ground to the excited state (the order can be shown to be rising from 1.058 to 1.159). This leads to an additional bathochromic shift of the fluorescence peak and in turn to a higher Stokes shift moving the emission maximum closer to the highest sensitivity position of the photodetector.

On the contrary, Chromophore II (FIG. 1) is localized mainly within the phenyl unit in position 5 of the pyrazoline cycle. The unit is not conjugated with the auxochromic N(1) atom and the total length of $\pi$-conjugation becomes shorter than in chromophore I. Moreover, the phenyl unit in position 5 is tilted to even higher angle with respect to the molecular plane (59 degrees) due to higher steric obstacles in this case. This leads to a shorter wavelength spectral position of the corresponding $\pi$-$\pi$* electron transition in comparison to the same transition in chromophore I. Interruption of the conjugation at N(1) adjacent phenyl makes the corresponding absorption spectrum similar to that of the toluene. Therefore, an additional absorption band, which belongs to the chromophore II, can overlap with the absorption band of the polymer matrix thus synergistically enhancing energy harvesting properties in system as the whole.

Reduced conjugation of the phenyl group in position 5 of TPhH allows chemical functionalization of the molecule without significant variation of the fluorescence spectral properties of the fluorophore or its analogs (e.g., PZ1-PZ3 described above). As such, this phenyl unit can be utilized in one embodiment for modification that can provide covalent bounding to polymer chains.

As described in more detail in the Examples section, higher Stokes shifts are found in disclosed fluorophores in comparison to $\alpha$NPO and other commercially available scintillators. This is evidence of the ease of energy exchange of the disclosed fluorophores with the environment. Higher Stokes shift also leads to reduction of self-filtering (self-absorption) process, i.e. to an enhanced brightness of the emission.

As mentioned above, disclosed fluorophores can be nonplanar. It is generally believed (based on numerous experimental studies and quantum mechanical calculations) that planar conjugated structures have an advantage of higher $\pi$-electron delocalization and so are generally desirable for more efficient fluorophores. However, as discussed above, the TPhP structure is essentially nonplanar. While this fact reduces to some extend photoluminescence properties it is favorable for higher luminosity. Rotation of two phenyl units out of the main plane can create a 3D "antenna" with phenyl ring planes looking into three orthogonal directions. This structure can create a unique possibility for energy harvesting from the whole 360 degree steric angle around any particular fluorophore emitting center while a traditional 2D fluorophore has "dead zones" (i.e., exciton waves coming from the edge directions cannot excite the molecules). In addition, the existence of two almost independent chromophores within the disclosed fluorophore structure as discussed above can make spectral energy decoupling thus broadening the range of possible spectral range of the radiation to be captured. In other words, the pyrazoline-based fluorophores described herein can act as simultaneously the primary and the secondary fluorophores of a plastic scintillator, depending on the energy of the absorbed or transmitted radiation.

Yet another advantage of the disclosed fluorophore's non-planarity is the resulting hindering of the chromophore aggregation process. Aggregation can significantly reduce both fluorescence and luminosity yield due to self-quenching in the aggregates. In the case of planar aromatic molecules, formation of dimers and higher aggregates is very difficult (if possible at all) to avoid. On the other hand, steric restrictions naturally reduce the aggregation trend in the disclosed non-planar fluorophores. The process is confirmed by fluorescence spectra described further herein in which additional lines due to formation of aggregates do not appear.

Plastic scintillators disclosed herein can contain at least one of the disclosed fluorophore dissolved (i.e., not aggregated in a solid) in a polymeric matrix. The matrix polymer(s) can be any suitable polymer that possesses affinity to the fluorophore (to avoid aggregation of the latter) and high optical transparency in the visible range of light. In one embodiment, the polymeric matrix can include one or more aromatic polymers (e.g., polystyrene (PS), polyvinyltoluene (PVT), polyvinylcarbazole (PVK), etc.) due to a capability for excitonic (i.e., non-radiative) energy transfer. In one embodiment, polymers of the matrix can be crosslinked, which can provide higher mechanical stability to the plastic scintillator.

In one embodiment, in addition to one or more of the disclosed fluorophore molecules, a plastic scintillator can include one or more secondary fluorophores or wavelength shifters as are known in the art that can be used to adjust the emitted light wavelength to the maximum spectral sensitivity of the receiving photodetector (photo-multiplying tube or semiconductor device).

In one particular embodiment, a plastic scintillator can include a polystyrene-based matrix that can include at least one polystyrene (e.g., polystyrene (PS) or a derivative thereof as is known in the art) in the matrix. As is known, polystyrenes can exhibit high optical transparency as well as energy absorption in deep UV (e.g., about 250-280 nm) and efficient exciton energy transfer mechanism through interacting aromatic rings of the polymer. Polystyrene-based materials may be particularly beneficial due to the particular architecture of the pyrazoline unit that provides two independent chromophores as discussed above. More specifically, in one embodiment, one of the chromophores of the fluorophore can absorb in the UV with a broad absorption range close to the band gap energy of polystyrene, which can make polystyrene-based matrices particularly attractive in some embodiments.

To form a plastic scintillator, the fluorophore(s) can be introduced into the matrix in any fashion as is generally known in the art. For instance, in one embodiment the fluorophore(s) can be blended (and optionally bonded) with monomers prior to polymerization of the monomers. In another embodiment, a preformed polymeric resin can be saturated with the fluorophores via swelling of the polymer matrix in a solution comprising the fluorophore(s). In this approach, fluorophore molecules can diffuse into the matrix driven by a concentration gradient, optionally in conjunction with additional external pressure or other driving force, and can be trapped (and optionally bonded) in the matrix as the structure dries following the swelling stage.

Beneficially, due to the high photoluminescence and high luminosity of the fluorophores, the can be incorporated into a polymeric matrix in a reduced amount as compared to other, previously known fluorophores. For instance, a plastic scintillator can include a fluorophore in an amount of about 3 w/w % or less, or about 1 w/w % or less in some embodiments, for instance from about 0.1 w/w % to about 0.5 w/w % in some embodiments.

In a typical scintillator formation process, the final concentration of the fluorophores in the scintillator can be difficult to control, for instance due to fluorophore leaching during suspension polymerization or solvent washing procedures. However, in one embodiment, the fluorophore can include a reactive functionality, e.g., a vinyl functionality as described above. In this embodiment, the fluorophore can bond with a polymer of the matrix, either as a co-monomer during polymer synthesis or in a second stage reaction following polymerization. As such, the fluorophore can be covalently bonded to a polymer of the matrix and the concentration can be precisely controlled and can remain essentially unaffected during resin washing.

Disclosed fluorophores and plastic scintillators can be utilized in a wide variety of applications including, without limitation, as radioactivity (e.g., neutron and gamma ray) detectors (for instance in homeland security), as fluorescent inks in security printing applications, in biological tagging applications, in physics and astronomy applications as nuclear particle and gamma ray detectors, and in environmental hazard detection and monitoring, just to name a few.

The present disclosure may be better understood with reference to the Examples set forth below.

Example

Materials

All chemicals were used as received except monomers, which were disinhibited by passing through a column of basic alumina before use. 9,10-Diphenylanthracene, 1-methyl-2-pyrrolidinone, and silica-gel were from Alfa Aesar (USA). Tris(dibenzylideneacetone)dipalladium(0) ($Pd_2(dba)_3$) was from Tokyo Chemical Industry Co. (Japan). Cyclohexane, tributyl(vinyl)tin, $CDCl_3$, and methyl acetate were obtained from Acros Organic (USA). Sodium sulfate and ammonium chloride were from J. T. Baker (USA). Ethanol and methanol were purchased from BDH (UK). 4-methylstyrene monomer, divinylbenzene (DVB), azobisisobutyronitrile (AIBN), toluene, poly(vinyl alcohol) (PVA, average MW 65,000-124,000 Da, degree of hydrolysis 87-89%), tri(2-furyl)phosphine, 4-ethylacetophenone, 4-bromobenzaldehyde, 4-fluorobenzaldehyde, phenylhydrazine (PHZ), acetic acid, 2-propanol and 4-chloromethylstyrene (CMS) were from Sigma-Aldrich. Reagent grade NaCl, diethyl ether, dimethylformamide (DMF), chloroform and hexane were from Fisher Scientific. Hydroxypropyl methylcellulose (HPMC) was from Dow Chemical Co. (USA).

Instrumentation

All $^1H$ and $^{13}C$ NMR spectra were recorded on a JEOL ECX-300 spectrometer operating at 300 MHz for $^1H$ NMR and 75 MHz for $^{13}C$ NMR at room temperature in $CDCl_3$ solvent. The chemical shifts (δ) are reported in ppm and were referenced to the residual solvent peak. The coupling constants (J) are quoted in Hz. A Cary 50 Bio UV-Vis spectrophotometer (Varian, Australia Pty Ltd) was used for absorption spectra measurements. All FTIR spectra were collected using a Thermo Nicolet 6700 FTIR spectrometer (Thermo Scientific; 128 scans, 4 cm-1 resolution). Fluorescence was measured using PTI QuantaMaster 60 spectrofluorometer systems (Photon Technology International, Inc) in the range of 300-600 nm. The Raman spectrometer consisted of an Innova 200 argon ion laser (514.5 nm wavelength at about 1 mW) and a Triplemate 1377 (Spex) spectrograph interfaced to a liquid nitrogen cooled Model LN1152 CCD detector (Princeton Instruments) operating at −120° C. The luminosity and scintillation efficiency of the plastic scintillator materials were quantified using a Hidex Triathler liquid scintillation counter (LSC) and luminometer (Lablogics, Inc., USA).

Organic Synthesis

Figure 2:
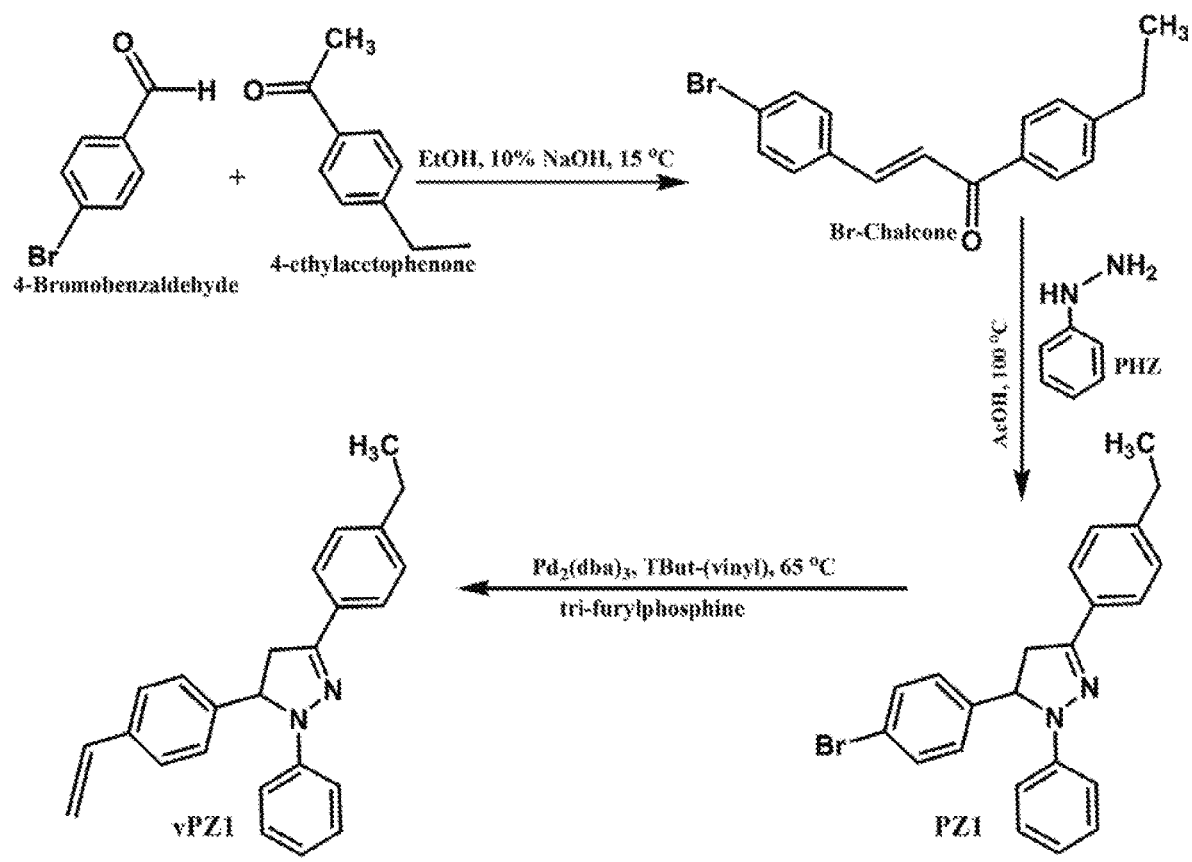
FIG. 2 presents one possible scheme for forming fluorophores as described herein.

The organic syntheses of 5-(4-bromophenyl)-3-(4-ethylphenyl)-1-phenyl-4,5-dihydro-1H-pyrazole (PZ1), and 3-(4-ethylphenyl)-5-(4-fluorophenyl)-1-phenyl-4,5-dihydro-1H-pyrazole (PZ2) were performed using two successive steps. 3-(4-ethylphenyl)-5-(4-vinylphenyl)-1-phenyl-4,5-dihydro-1H-pyrazole (vPZ1) was synthesized using PZ1 fluorophore as staring material and Stille cross coupling reaction, which has been reported successfully for other materials. Scheme 1 shown in FIG. 2 summarizes the organic synthesis routes of these three pyrazole derivatives. The 5-(furan-2-yl)-1-phenyl-3-(thiophen-2-yl)-4,5-dihydro-1H-pyrazole (PZ3) was obtained by reacting heterocyclyl-substituted α,β-unsaturated ketones with phenylhydrazine (see, Chem. Ber. 1957, 90, 2707-2711). PZ fluorophores were synthesized using chalcones as intermediate materials.

(E)-3-(4-Bromophenyl)-1-(4-ethylphenyl)prop-2-en-1-one (Br-chalcone)

Equimolar amounts of 4-ethylacetophenone and 4-bromobenzaldehyde were mixed in 10 ml of ethanol at 15±2° C. with 5 ml of 10% NaOH solution to prepare the Br-chalcone. After 1 hour stirring the Br-chalcone precipitate was filtered, washed with DDI water until neutral pH. The precipitate was filtered, dried and recrystallized from methanol (yield, 76%). 1H NMR (300 MHz, acetone-d6) 1.270 ($t_{J=7.2\ Hz}$, 3H, $CH_3$ (Et)), 2.755 ($q_{J=7.2\ Hz}$, 2H, $CH_2$ (Et)), 7.426 ($d_{J=8.1\ Hz}$, 2H, Ar—H (4'-Et)), 7.665 ($d_{J=8.7\ Hz}$, 2H, Ar—H (4-Br)), 7.754 ($d_{J=16.2\ Hz}$, H, α-H— chain), 7.828 ($d_{J=8.7\ Hz}$, 2H, Ar—H (4-Br)), 7.952 ($d_{J=15.9\ Hz}$, H, α-H-chain), 8.109 ($d_{J=8.4\ Hz}$, 2H, Ar—H (4'-Et)). Anal. Calcd $C_{17}H_{15}BrO$: C, 64.77; H, 4.80; Br, 25.35. Found: C, 64.85; H, 4.77; Br, 25.69%. Melting Point 96-97° C.

(E)-3-(4-Fluorophenyl)-1-(4-ethylphenyl)prop-2-en-1-one (F-chalcone)

Using the same reaction, 4-fluorobenzaldehyde and 4-ethylacetophenone reacted in a mixed solvent of ethanol and 10% NaOH. The product was F-chalcone which was treated as was applied for Br-chalcone (yield, 68%). $^1H$ NMR (300 MHz, acetone-$d_6$) 1.269 ($t_{J=7.8\ Hz}$, 3H, $CH_3$ (Et)), 2.753 ($q_{J=7.8\ Hz}$, 2H, $CH_2$ (Et)), 7.257 (dd,$_{J=8.4\ Hz}$, 2H, Ar—H (4-F), 7.422 ($d_{J=8.7\ Hz}$, 2H, Ar—H (4'-Et)), 7.782 ($d_{J=15.9\ Hz}$, H, β-H-chain), 7.878 ($d_{J=15.3\ Hz}$, H, α-H— chain), 7.915-7.963 (m, 2H, Ar—H (4-F), 8.105 ($d_{J=7.8\ Hz}$, 2H, Ar—H (4'-Et). Anal. Calcd $C_{17}H_{15}FO$: C, 80.29; H, 5.94. Found: C, 80.20; H, 5.96%. Melting point 93-94° C.

5-(4-Bromophenyl)-3-(4-ethylphenyl)-1-phenyl-4,5-dihydro-1H-pyrazole (PZ1)

A mixture including 0.63 g (0.2 mmol) of the compound (E)-3-(4-bromophenyl)-1-(4-ethylphenyl)prop-2-en-1-one and 0.3 g (0.3 mmol) of phenylhydrazine was heated in 5 ml acetic acid for 1 h at (100±5)° C. The solid product was filtrated and recrystallized from 2-propanol, 0.6 g (74.1%). IR, vmax $cm^{-1}$ 2959, 1596, 1498, 1392, 1328, 1125, 1072, 873, 816, 752; $^1H$ NMR (300 MHz, $CDCl_3$) δ 7.64 (d, $_{J=8.3\ Hz}$, 2H), 7.54-7.40 (m, 2H), 7.30-7.14 (m, 6H), 6.80 (ddd, $_{J=7.2,\ 1.8,\ 0.9\ Hz}$, 1H), 5.21 (dd, $_{J=12.3,\ 7.1\ Hz}$, 1H), 3.82 (dd, J=$_{17.1,\ 12.3\ Hz}$, 1H), 3.09 (dd, J=$_{17.1,\ 7.1\ Hz}$, 1H), 2.68 (q, J=$_{7.6\ Hz}$, 2H), 1.35-1.17 (m, 3H).

$^{13}C$ NMR (76 MHz, $CDCl_3$) δ 152.3, 144.5, 143.0, 139.9, 131.8, 130.3, 129.6, 129.2, 128.3, 127.8, 126.0, 125.5, 122.7, 105.3, 28.8, 15.6. Mp 154-155° C. Anal. Calcd $C_{23}H_{21}BrN_2$: C, 68.15; H, 5.22; Br, 19.71; N, 6.91. Found: C, 68.35; H, 5.28; Br, 19.62; N, 6.83%.

3-(4-Ethylphenyl)-5-(4-fluorophenyl)-1-phenyl-4,5-dihydro-1H-pyrazole (PZ2)

A mixture of the compound (E)-3-(4-fluorophenyl)-1-(4-ethylphenyl)prop-2-en-1-one 0.45 g (0.18 mmol) and 0.5 g (0.46 mmol) of phenylhydrazine was heated in 4 mL acetic acid for 2 h at (100±5)° C. The reaction mixture was diluted with water and the gummy precipitate was treated with hot methanol. The precipitated powder was filtered off and recrystallized from methanol, then the solid product was filtrated and recrystallizated from 2-propanol, 0.35 g (57.4%). IR, $v_{max}$ $cm^{-1}$ 2960, 1590, 1500, 1395, 1327, 1218, 1128, 996, 829, 743, 690; $^1H$ NMR (300 MHz, $CDCl_3$) δ 7.74 (dd, $_{J=57.5,\ 7.9\ Hz}$, 2H), 7.42-7.12 (m, 6H), 7.03 (ddd, $_{J=15.7,\ 9.9,\ 4.9\ Hz}$, 4H), 6.86-6.69 (m, 1H), 5.24 (dd, $_{J=12.2,\ 7.1\ Hz}$, 1H), 3.82 (dd, $_{J=17.1,\ 12.3\ Hz}$, 1H), 3.09 (dd, $_{J=17.1,\ 7.1\ Hz}$, 1H), 2.78-2.54 (m, 2H), 1.32-1.15 (m, 3H). $^{13}C$ NMR (76 MHz, $CDCl_3$) δ 164.4, 161.1, 152.1, 144.5, 143.5, 139.8, 130.7, 129.1, 128.3, 127.8, 126.0, 125.5, 115.9, 115.6, 28.8, 15.6. Mp 133-134° C. Anal. Calcd $C_{23}H_{21}FN_2$: C, 80.21; H, 6.15; N, 8.26. Found: C, 80.12; H, 6.25; F, 5.52; N, 8.13%.

3-(4-Ethylphenyl)-5-(4-vinylphenyl)-1-phenyl-4,5-dihydro-1H-pyrazole (vPZ1)

5-(4-bromophenyl)-3-(4-ethylphenyl)-1-phenyl-4,5-dihydro-1H-pyrazole (PZ1) (1250 mg, 3.59 mmol), tris(dibenzylideneacetone)dipalladium(0) [120 mg, 131 μmol (5 mol % Pd)], and tri-2-furylphosphine [190 mg, 820 μmol (20 mol % ligand)] were stirred in 1-methyl-2-pyrrolidinone (50 mL) for 15 min. Tributyl(vinyl) tin (1260 μL; 1367 mg, 4.31 mmol) was added, and the resultant mixture was heated to 65° C. and stirred for 48 h, after which time blackening of the mixture had occurred. The reaction mixture was then stirred with 1 M NaOH for 30 min before being filtered through No. 1 Whatman filter paper. The liquid phase was separated and extracted with 5% (v/v) chloroform in diethyl ether (3×50 mL). The combined organic extracts were washed with a saturated aqueous solution of ammonium chloride (4×25 mL), dried over sodium sulfate, and concentrated under reduced pressure to give a crude green solid. Flash chromatography (20% (v/v) chloroform in hexane) gave 3-(4-ethylphenyl)-5-(4-vinylphenyl)-1-phenyl-4,5-dihydro-1H-pyrazole (vPZ1) as light green crystals (1000 mg, 98.2%). IR, $V_{max}$ $cm^{-1}$ 3088, 2959, 2859, 1596, 1498, 1392, 1328, 1208, 1129, 1012, 911, 828, 737; 1H NMR (300 MHz, $CDCl_3$) δ 7.70 (d, $_{J=6.7\ Hz}$, 2H), 7.49-7.01 (m, 10H), 6.90-6.60 (m, 2H), 5.77 (d, $_{J=17.6\ Hz}$, 1H), 5.28 (t, $_{J=8.3\ Hz}$, 2H), 3.86 (dd, $_{J=16.3,\ 13.1\ Hz}$, 1H), 3.16 (dd, $_{J=17.0,\ 7.2\ Hz}$, 1H), 2.72 (q, $_{J=7.5\ Hz}$, 2H), 1.30 (td, $_{J=7.5,\ 1.6\ Hz}$, 3H). $^{13}C$ NMR (76 MHz, $CDCl_3$) δ 152.2, 144.2, 140.3, 137.5, 136.0, 130.5, 130.0, 129.0, 128.2, 127.5, 126.4, 125.9, 125.5, 114.8, 105.1, 28.8, 15.6.

5-(Furan-2-yl)-1-phenyl-3-(thiophen-2-yl)-4,5-dihydro-1H-pyrazole (PZ3)

PZ3 fluorophore was prepared by reacting heterocyclyl-substituted α,β-unsaturated ketones with phenylhydrazine. The chemical analysis of PZ3 showed that its formula is $C_{17}H_{14}N_2OS$; molecular weight is 294.37 and melting point is 139° C. IR, $v_{max}$ cm$^1$ 3089, 1594, 1496, 1378, 1307, 1149, 1013, 946, 855, 735, 716, 693; 1H NMR (300 MHz, CDCl3) δ 7.39-7.28 (m, 2H), 7.28-7.17 (m, 2H), 7.17-7.06 (m, 3H), 7.07-6.96 (m, 1H), 6.88-6.73 (m, 1H), 6.33-6.17 (m, 2H), 5.34 (dd, $_{J=12.1,\ 6.8\ Hz}$, 1H), 3.71 (dd, $_{J=16.8,\ 12.0\ Hz}$, 1H), 3.37 (dd, $_{J=16.8,\ 6.8\ Hz}$, 1H).

Resin Preparation, Functionalization and Stability

Scintillating polymer resins were prepared as ca. 100-400 μm diameter spherical beads via a suspension polymerization technique. A mixture of styrene or 4-methylstyrene monomer with 4-chloromethyl styrene (CMS), DVB (cross-linker), AIBN (initiator) and a toluene porogen was used as a dispersed oil phase. The ratio of the components was varied to adjust the porosity, optical transparency and size of the final polymer beads. The dispersed phase contained also 0.5% (w/w) of organic fluorophores: PZ1, PZ2, PZ3 or vPZ1. A continuous aqueous phase contained PVA, NaCl and HPMC as emulsion stabilizers.

The efficiencies of incorporation of the fluorophores into the polymer beads were estimated using two different steps. 1) To washout all un-polymerized fractions, 1 gram of each of the four polymers (P-PZ1, P-PZ2, P-PZ3 or P-vPZ1) was mixed with 15 mL of an organic solvent (methyl acetate) and left overnight on an end-over-end stirrer, the resin was filtered and further washed with fresh solvent to remove any surface impurities; organic leachates were tested using UV-Vis absorbance. 2) The luminosities of the unwashed and washed polymer beads were measured using about 25 mg of the scintillating beads in 7 mL LSC vial. 1 μCi $^{241}$Am point source was positioned at about 0.5 cm above the bead surface and the light output from α particles deposition was measured using a Hidex Triathler LSC.

Fluorescence properties of organic fluorophores in cyclohexane and toluene solvents were studied using a double-monochromator spectrofluorometer system to eliminate background signal and minimize noise due to stray light. To study fluorophore solutions, a 3 mL square cross-section quartz cuvette was used to hold a solution with a typical fluorophore concentration of 1 mg/mL in each solvent. The quartz cuvette was placed in a vertical position with the cuvette cross-section at 45° angles both to the incident light beam and to the PMT slit directions. The molar extinction coefficient of PZ1, PZ2, PZ3 and vPZ1 in cyclohexane or toluene was measured using UV-Vis, while the corresponding fluorescence quantum yield was calculated relative to 9,10-diphenylanthracene (DPA) as a reference material.

Results

Figure 3:
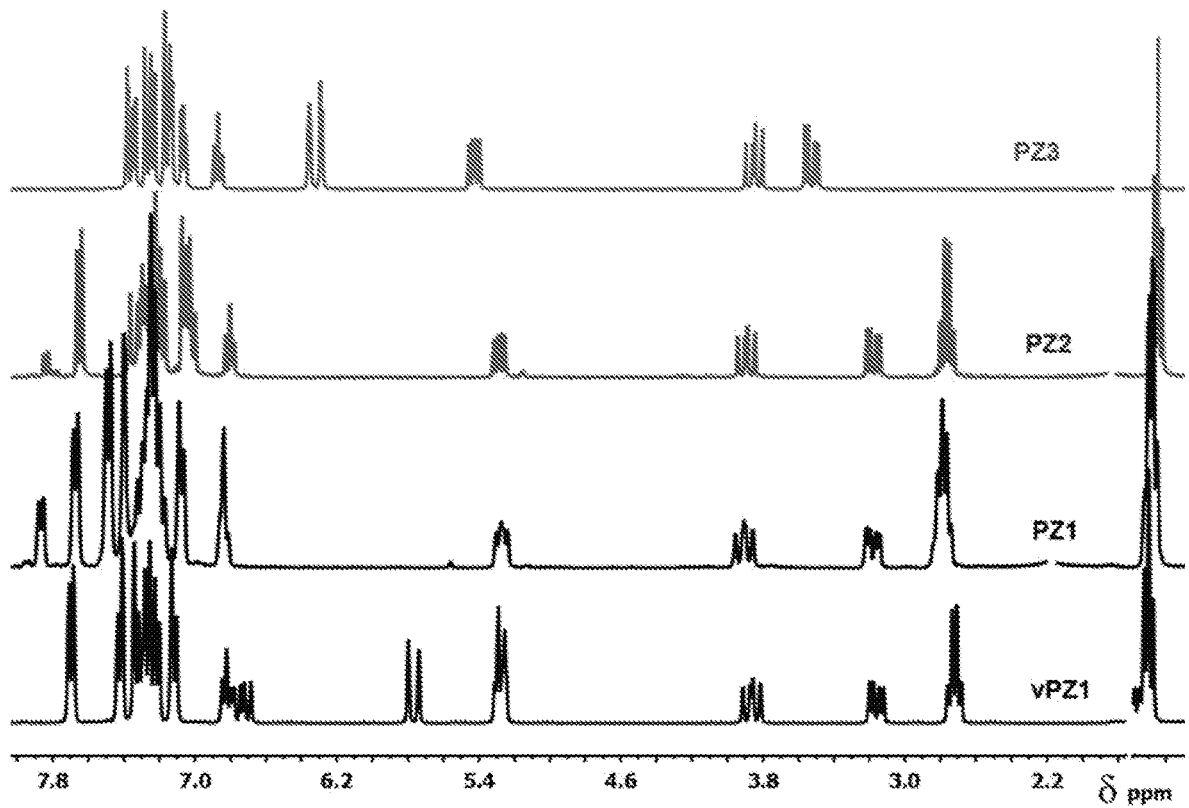
FIG. 3 presents the NMR spectra for four exemplary fluorophores (PZ3, PZ2, PZ1, and vPZ1) as described herein.

FIG. 3 shows typical $^1$H NMR spectra of PZ1, vPZ1, PZ2 and PZ3 in CDCl$_3$ with signal assignment for comparison. The figure confirms the successful organic synthesis of PZ1 and vPZ1 as related reactant and product materials, respectively. The $^1$H and $^{13}$C peak positions and integrations for each material were configured using the capability of the Mestrenova software to predict NMR spectra after introducing the chemical structure of final products. In almost all cases, the modeled and experimental gave comparable results that helped to confirm the chemical structure of the synthesized fluorophores. Comparing the $^1$H NMR spectra of PZ1, vPZ1 and PZ2, the peak corresponding to the 3 protons of the pyrazole group appeared between 3.0 and 5.5 ppm. They had identical position in PZ1 and PZ2, while have small shift in the vPZ1 where the peaks positions changed from 3.09, 3.82 and 5.21 to 3.16, 3.86 and 5.25, respectively. The peaks show around 1.25 and 2.7 ppm assigned to the hydrogens in —CH$_3$ and —CH$_2$— of the ethyl group in the three PZ materials locate around 1.25 ppm for the three materials. The $^1$H NMR spectrum of the vPZ1 showed three new peaks between 5 and 6.75 ppm: two peaks at 5.25 and 5.77 ppm assigned to the chemical shift of hydrogen in —CH$_2$ of the vinyl group and one peak at 6.73 ppm assigned to the —CH proton of the same vinyl group. The PZ3 has three different cyclic groups, which have specific peaks positions. $^1$H NMR spectrum showed that the three peaks assigned to chemical shift of protons in pyrazole group appear at 3.37, 3.71 and 5.34 ppm. Two protons of the furan group appeared at 6.28 ppm, while the peak at 7.14 ppm was assigned to one proton of the thiophene group. The 5 protons assigned for the phenyl group are between 6.75 and 7.5 ppm, also two thiophene protons and one furan proton locate within the same range. The total peaks integration in the synthesized PZ materials relative to the area of one stable proton revealed that the chemical conversions were almost 100%.

$^{13}$C NMR was further utilized to study the structure of PZ1, vPZ1, PZ2 and PZ3, using CDCl$_3$ as the chemical shift reference, which gives a strong signal at 77.2 ppm. The data analysis revealed that for PZ1, vPZ1 and PZ2, ethyl group carbons appeared as two peaks around 15.6 ppm for —CH$_3$ and 28.8 ppm —CH$_2$— of the same group. The three carbons of the pyrazole group appeared around 105.3, 122.7 and 152.3 ppm in the PZ1, while appeared at close positions for vPZ1 and PZ2 (105, 115 and 152 ppm). The aromatic carbons of the phenyl groups appeared as multiple signals between 125 and 145 ppm. The vPZ1 spectrum showed two new peaks at 125.5 and 137.5 ppm assigned to the attached vinyl group and corresponding to —CH$_2$ and —CH—, respectively. For PZ3, three peaks appeared at 103.3, 109.2 and 147.5 ppm assigned for pyrazole group. The furan group had four peaks at 111.4, 124.4, 140.1 and 144.3 ppm and 144.3 ppm, while the thiophene group had three peaks at 127.6, 128.8 and 136 ppm. Finally, the high intense peaks at 125, 126.2, 129.2 and 142.7 were assigned to carbons of the phenyl group.

Figure 4:
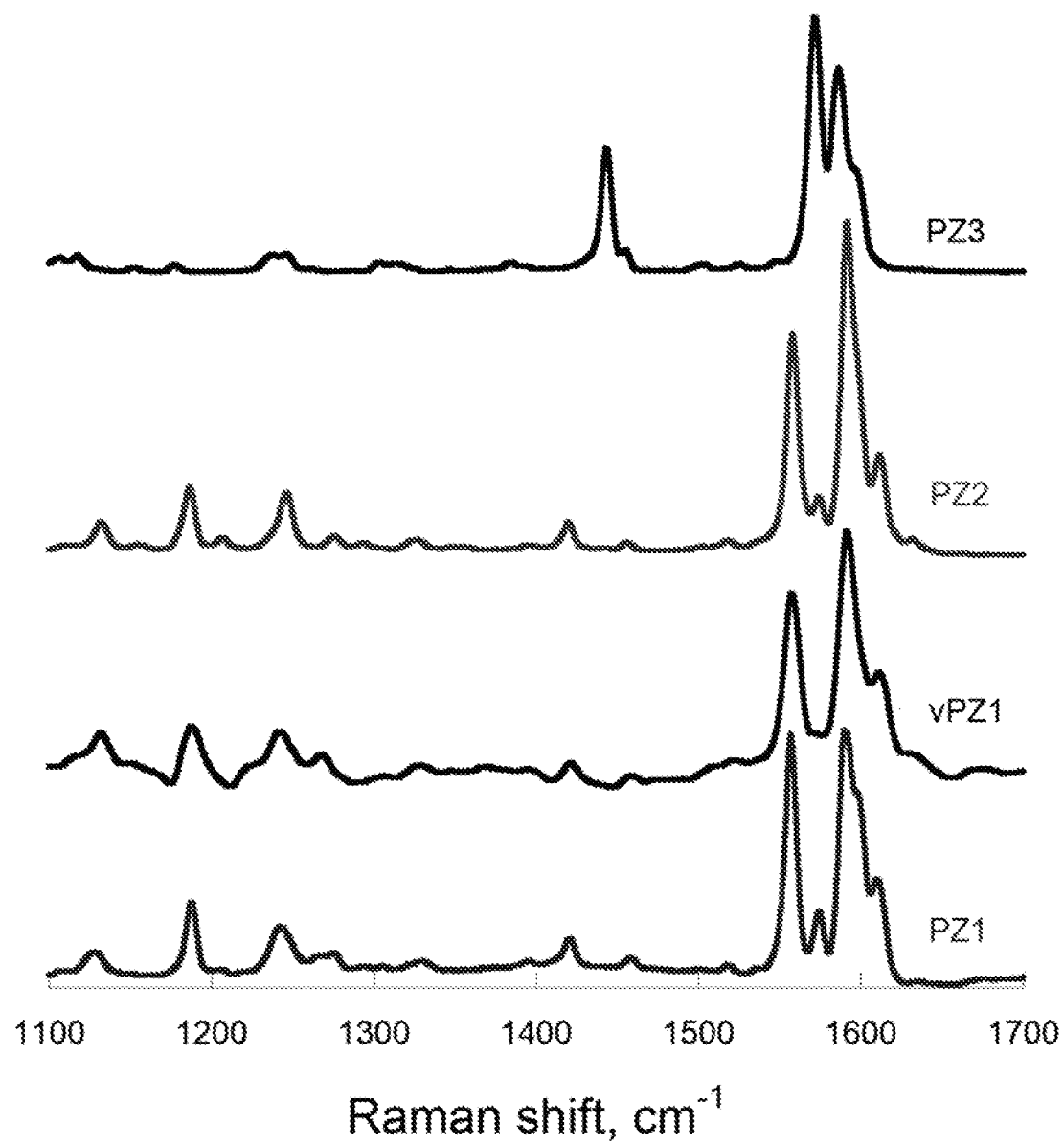
FIG. 4 presents the Raman spectra of the four exemplary fluorophores of FIG. 3.

Raman spectra for the molecules are shown in FIG. 4. PZ1 and PZ2 molecule vibrations were almost identical, which is natural considering similarity of their chemical structure. vPZ1 had an additional characteristic band at 1630 cm$^{-1}$ (arrow) corresponding to vinyl carbon stretching vibration and therefore confirmed successful modification of the original PZ1 to introduce this functionality. PZ3 Raman spectrum was significantly different from the other three spectra and corresponded to the difference in the fluorophores' structure (i.e., presence of thiophene/furan rings instead of differently substituted phenyls).

Figure 5:
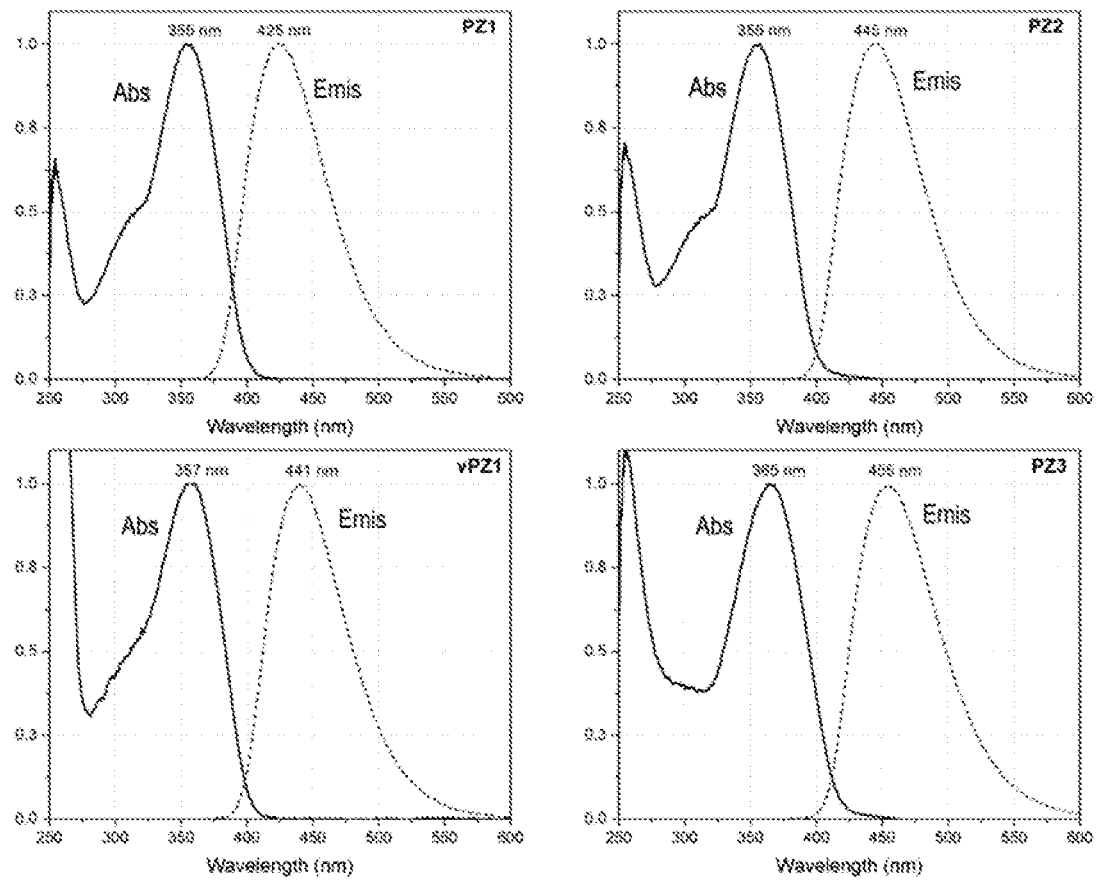
FIG. 5 presents the absorption and emission spectra for the four exemplary fluorophores of FIG. 3 in methyl acetate solution (0.022 mM). All spectra are normalized to the corresponding maxima around 360 nm (absorption) and 425, 445, 441, or 455 nm (emission). The emission scans were recorded with the excitation wavelength of 360, 360, 360 and 370 nm for PZ1, PZ2, vPZ1, and PZ3 fluorophores respectively, which correspond to the maximum of the emission in each case.

Spectral properties of the fluorophores in methyl acetate solution are shown in FIG. 5. The spectra were normalized to the corresponding maxima for fair comparison. The absorption spectra show two well pronounced maxima: a sharp peak at around 260 nm and a broad peak at around 350-360 nm. The absorption peak at 260 nm perfectly matches phenyl ring excitation of the polymer matrix. This is evidence that high energy photons or energetic particles can deposit their energy to the matrix, which is followed by energy cascading and transfer as an excitation wave to the fluorophore. The latter can be excited with high probability and then relaxes to the ground state through emission of visible light photon.

Depending on the fluorophore, the ratio between the two peaks varied from 0.6 to 1.5 with the smallest one observed in PZ1 and highest for vPZ1. During fluorescence measurements several excitation wavelength and several fluorophore concentrations (0.0055 mM, 0.011 mM and 0.022 mM) were examined. The presented emission spectra of FIG. 5 correspond to the highest emission intensity, however, the position of the maximum did not depend on the excitation wavelength and was independent on the concentration in the considered range. The emission spectra showed a simple shape, which evidences absence of a significant fluorophore aggregation.

Figure 6:
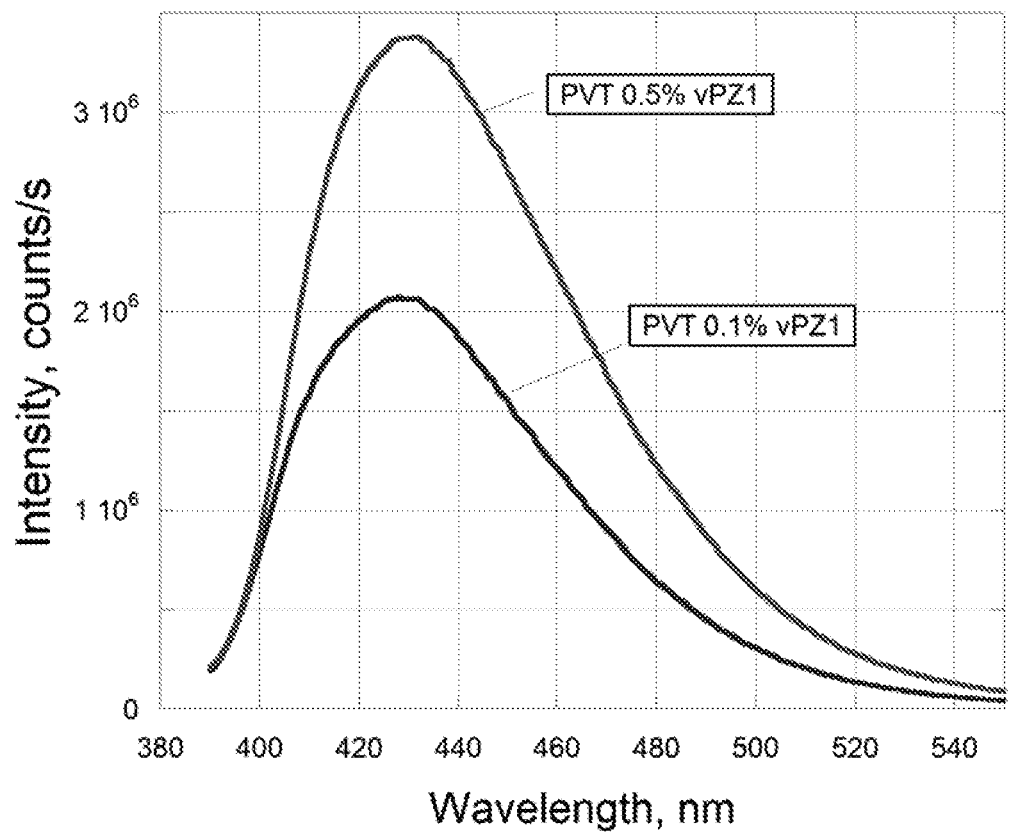
FIG. 6 presents fluorescence spectra of polymeric beads containing vPZ1 or vNPO fluorophores with regard to the fluorophore concentration (excitation wavelength is shown for each spectrum).

FIG. 6 shows fluorescence properties of the PZ fluorophores incorporated in a polymer matrix. As can be seen, the spectra show a drastic difference in the fluorescence intensity of the vPZ1 in comparison to 2-(1-naphthyl)-4-vinyl-5-phenyloxazole (vNPO), which was used as a representative example of traditional scintillating fluorophores. 200-400 μm in diameter PVT beads with just 0.1% concentration of vPZ1 show at least twice higher integral fluorescence intensity in comparison to the same polymer beads prepared five times higher concentration of vNPO fluorophores. This difference can be clearly observed even with a naked eye under illumination of the resins with a 395 nm wavelength source. If the concentration of the fluorophores is the same, the observed advantage in the integral intensity is even more exciting reaching 3-5 times depending on the size of the beads (higher difference is observed for smaller bead's diameter). Also noted is an 11 nm hypsochromic shift observed for the fluorescence peak in PVT matrix in comparison to methyl acetate (MeAc) solution. Similar effect has been reported for other fluorophores confined within nanopores of PS matrix.

Figure 7:
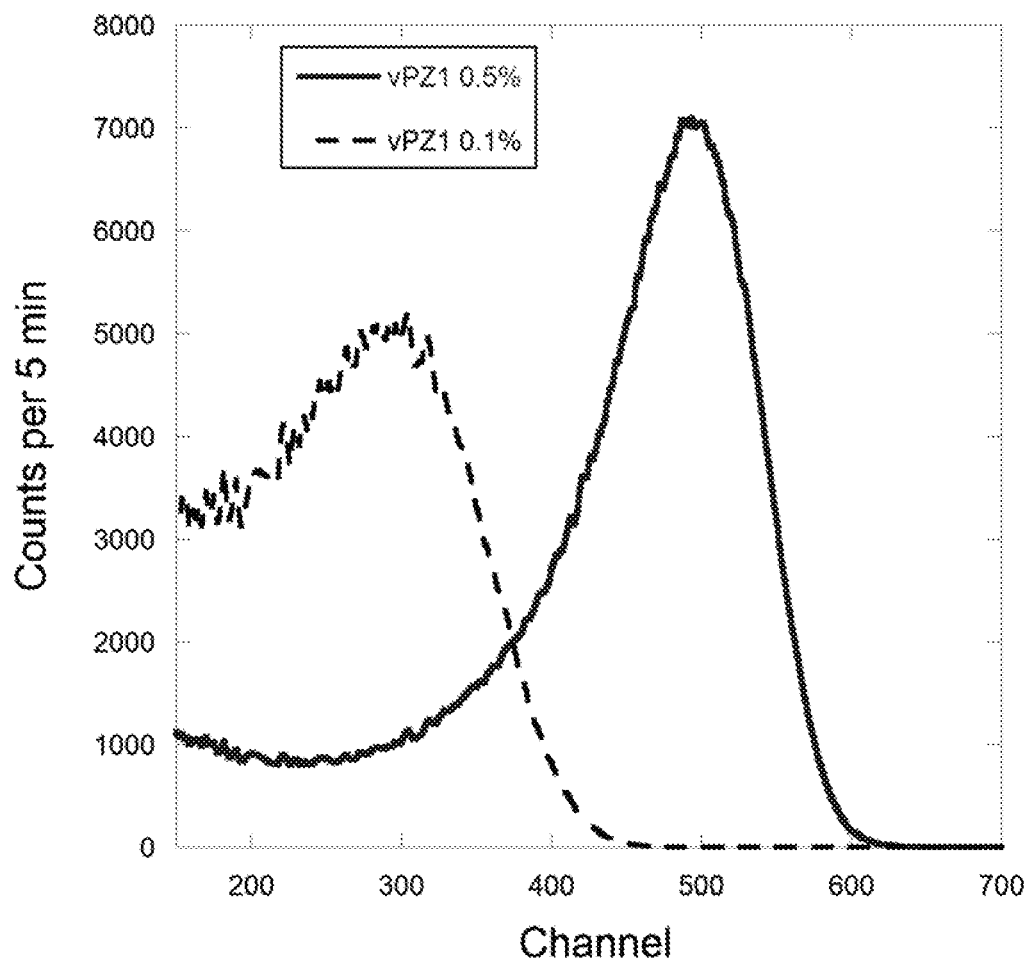
FIG. 7 presents the radioluminosity spectra of PVT beads containing (a) vPZ1 or (b) vNPO and αNPO fluorophores depending on the fluorophore concentration.

FIG. 7 demonstrates the advantage of PZ fluorophores in scintillator applications (only vPZ1 fluorophore is presented in FIG. 7, however, all PZ fluorophores were tested and showed high luminosity). As can be seen, the maximum was well pronounced and shifted to higher channel number even at a minute concentration of vPZ1 in comparison to a six times higher concentration of vNPO. Optical properties of PZ fluorophores in different matrices in comparison to commonly used commercial αNPO fluorophore are summarized in Table 1.

Measurements demonstrated a superior brightness of the synthesized fluorophores in comparison to the DPA standard. Functionalization of PZ1 molecules with vinyl groups decreased the φ value to ~75%. Performance of vPZ1 fluorophore in the polymer matrix was significantly improved in comparison to the solution state. Thus, αNPO and vNPO fluorophores had higher φ than vPZ1 in solution: ~100% versus 74-79%. In the solid PS or PVT matrix the situation was reversed and the integral photoluminescence intensity of vPZ1 exceeded by at least three times that of the NPO fluorophores at the same concentration (FIG. 6). This confirmed the importance of the exciton transfer process through the matrix for the overall scintillation performance in the system.

While certain embodiments of the disclosed subject matter have been described using specific terms, such description is for illustrative purposes only, and it is to be understood that changes and variations may be made without departing from the spirit or scope of the subject matter.

What is claimed is:

1. A plastic scintillator comprising a polymeric matrix and a 1,3,5-triaryl substituted pyrazoline incorporated in the polymeric matrix, wherein the 1,3,5-triaryl substituted pyrazoline is bonded to a chain of a polymer of the polymeric matrix via reaction of a reactive functional group of the pyrazoline with a reactive group of the polymer or via reaction of a bifunctional crosslinking agent with a reactive functional group of the pyrazoline and with a reactive group of the polymer.

2. The plastic scintillator of claim 1, wherein the 1,3,5,-triaryl substituted pyrazoline has the following structure:

TABLE 1

| Fluorophore | $\lambda_A$(nm)[a] | | $\lambda_E$(nm) | | $\Delta v$ (cm$^{-1}$)[b] | | $\varepsilon$ (L mol$^{-1}$ cm$^{-1}$)[c] | | $\phi$[d] | |
|---|---|---|---|---|---|---|---|---|---|---|
| | MeAc | PVT | MeAc | PVT | MeAc | PVT | Cyhex | Toluene | Cyhex | Toluene |
| PZ1 | 354 | 380 | 425 | 430 | 4719 | 3060 | 17073 | 18977 | 109 | 116 |
| vPZ1 | 357 | 380 | 441 | 430 | 5335 | 3060 | 15306 | 19087 | 74 | 79 |
| PZ2 | 355 | 391 | 445 | 433 | 5697 | 2481 | 17940 | 20428 | 107 | 114 |
| PZ3 | 365 | 398 | 455 | 448 | 5419 | 2804 | 16523 | 18531 | 111 | 116 |

[a]$\lambda_A$ and $\lambda_E$ are maximum absorption and emission wavelengths for organic fluorophores and corresponding polymer
[b]Stokes shift; $\Delta v = 1/\lambda_A - 1/\lambda_F$ in cm$^{-1}$
[c]$\varepsilon$ is molar absorptivity
[d]$\phi$ is the fluorescence quantum yield relative to 9,10-Diphenylanthracene (DPA)
cyhex: cyclohexane As can be seen, the PZ fluorophores exhibit broader absorption and emission bands, larger Stokes shift and higher energy luminosity response. The larger Stokes shift can reduce the probability of self-absorption of the emitted radiation and indicates a significant phonon interaction with the matrix. A simple photoluminescence quantum yield (φ) calculation can be based on comparison of the integral fluorescence intensity (I) and absorptivity (A) measured for solutions with the same low concentration and under the same experimental conditions (the same cuvette, solution volume, slits etc.) for the reference sample (ref) with known φ and a new sample (s) in accordance to: $\phi_s = \phi_{ref} \times (A_{ref} \times I_s)/(A_s \times I_{ref})$. 9,10-diphenylanthracene (DPA) fluorophore has the φ value close to 100% in accordance to previous publications and was used as a reference standard.

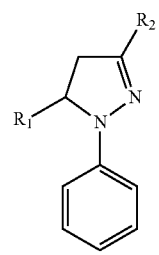

in which

R$_1$ and R$_2$ are independently selected from a heteroaryl group including one or more of an oxygen, selenium, or sulfur atom in the ring; an aryl halide group; or a phenyl alkyl including a C1 to C18 saturated or unsaturated alkyl that optionally includes a reactive functional group.

3. The plastic scintillator of claim 1, wherein the 1,3,5-triaryl pyrazoline has the following structure:

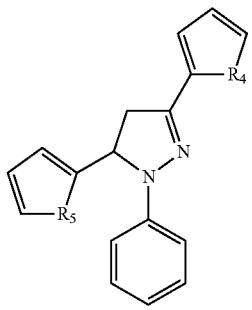

in which $R_4$ and $R_5$ are independently selected from sulfur, selenium and oxygen.

4. The plastic scintillator of claim 3, wherein $R_4$ is sulfur and $R_5$ is oxygen.

5. The plastic scintillator of claim 1, wherein the 1,3,5-triaryl substituted pyrazoline has the following structure:

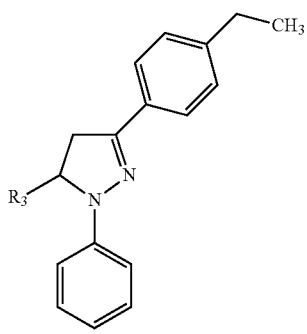

in which $R_3$ is an aryl halide group or a phenyl alkyl including a C1 to C18 saturated or unsaturated alkyl that optionally includes a reactive functional group.

6. The plastic scintillator of claim 5, wherein $R_3$ is an aryl bromide or an aryl fluoride.

7. The plastic scintillator of claim 6, wherein the scintillator has the following structure:

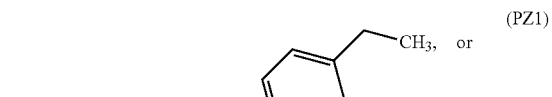
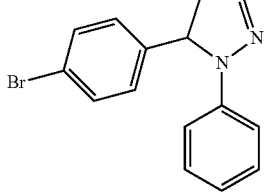

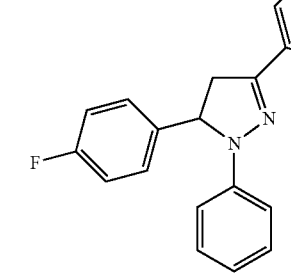

8. The plastic scintillator of claim 1, wherein the 1,3,4-triaryl substituted pyrazoline has been copolymerized with a monomer via chain polymerization or step polymerization.

9. The plastic scintillator of claim 1, wherein the polymeric matrix comprises a polystyrene.

10. The plastic scintillator of claim 1, wherein the polymeric matrix comprises a polyvinyltoluene or a polyvinylcarbazole.

11. The plastic scintillator of claim 1, further comprising a second fluorophore.

12. The plastic scintillator of claim 1, wherein the plastic scintillator is free of any secondary fluorophores.

* * * * *